United States Patent
Chebator et al.

(10) Patent No.: US 8,262,619 B2
(45) Date of Patent: Sep. 11, 2012

(54) INTRODUCER SHEATH FOR CATHETERS

(75) Inventors: Casey Chebator, Weymouth, MA (US); A. Ken Chan, Framingham, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/894,333

(22) Filed: Sep. 30, 2010

(65) Prior Publication Data

US 2012/0083740 A1  Apr. 5, 2012

(51) Int. Cl.
*A61M 5/178* (2006.01)

(52) U.S. Cl. .................. 604/164.05; 604/158
(58) Field of Classification Search ............ 604/103.04, 604/158, 164.05, 178, 180, 214, 250, 272; 606/108, 200
See application file for complete search history.

(56) References Cited

U.S. PATENT DOCUMENTS

| | | | |
|---|---|---|---|
| 668,879 A * | 2/1901 | Miller | 27/21.1 |
| 3,877,429 A * | 4/1975 | Rasumoff | 604/158 |
| 4,306,562 A | 12/1981 | Osborne | |
| 4,451,256 A * | 5/1984 | Weikl et al. | 604/164.03 |
| RE31,855 E | 3/1985 | Osborne | |
| 4,596,559 A | 6/1986 | Fleischhacker | |
| 4,747,833 A * | 5/1988 | Kousai et al. | 604/164.05 |
| 4,772,266 A | 9/1988 | Groshong | |
| 4,846,812 A | 7/1989 | Walker et al. | |
| 4,883,468 A | 11/1989 | Kousai et al. | |
| 4,950,257 A | 8/1990 | Hibbs et al. | |
| 5,098,392 A | 3/1992 | Fleischhacker et al. | |
| 5,104,388 A | 4/1992 | Quackenbush | |
| 5,125,904 A | 6/1992 | Lee | |
| 5,141,497 A | 8/1992 | Erskine | |
| 5,167,634 A | 12/1992 | Corrigan, Jr. et al. | |
| 5,221,263 A | 6/1993 | Sinko et al. | |
| 5,250,033 A | 10/1993 | Evans et al. | |
| 5,318,542 A | 6/1994 | Hirsch et al. | |
| 5,409,463 A | 4/1995 | Thomas et al. | |
| 5,441,504 A | 8/1995 | Pohndorf et al. | |
| 5,713,867 A | 2/1998 | Morris | |
| 5,752,937 A | 5/1998 | Otten et al. | |
| 5,951,518 A | 9/1999 | Licata et al. | |
| 6,027,480 A | 2/2000 | Davis et al. | |
| 6,033,388 A | 3/2000 | Nordstrom et al. | |
| 6,080,141 A | 6/2000 | Castro et al. | |
| 6,273,871 B1 | 8/2001 | Davis et al. | |
| 6,454,744 B1 | 9/2002 | Spohn et al. | |
| 6,641,564 B1 * | 11/2003 | Kraus | 604/164.1 |
| 6,645,178 B1 | 11/2003 | Junker et al. | |
| 6,663,595 B2 | 12/2003 | Spohn et al. | |
| 6,692,464 B2 | 2/2004 | Graf | |

(Continued)

OTHER PUBLICATIONS

European Search Report from European Application No. EP 11 18 3305 dated Nov. 28, 2011.

*Primary Examiner* — Victoria P Shumate
(74) *Attorney, Agent, or Firm* — Thomas M. Johnston, Esq.

(57) ABSTRACT

An introducer sheath includes a tubular body portion having a proximal region and a distal region, and defines an internal lumen configured and dimensioned to slidably receive a catheter. A penetrating portion at a distal end of the tubular body has a first tapered configuration to enlarge an opening in a body tissue during distal advancement of the introducer sheath through the body tissue and a second expanded configuration to enable the passage of a distal end portion of a catheter through the penetrating portion.

7 Claims, 5 Drawing Sheets

U.S. PATENT DOCUMENTS

| | | |
|---|---|---|
| 6,712,791 B2 | 3/2004 | Lui et al. |
| 6,796,991 B2 | 9/2004 | Nardeo |
| 6,808,509 B1 * | 10/2004 | Davey ................ 604/167.04 |
| 6,837,873 B1 | 1/2005 | Polley et al. |
| 6,939,327 B2 | 9/2005 | Hall et al. |
| 7,101,353 B2 | 9/2006 | Lui et al. |
| 7,192,433 B2 | 3/2007 | Osypka et al. |
| 7,316,667 B2 | 1/2008 | Lindstrom et al. |
| 7,422,571 B2 | 9/2008 | Schweikert et al. |
| 7,803,142 B2 * | 9/2010 | Longson et al. ............ 604/272 |
| 2001/0049499 A1 | 12/2001 | Lui et al. |
| 2003/0032941 A1 * | 2/2003 | Boyle et al. ................ 604/533 |
| 2003/0050604 A1 | 3/2003 | Lui et al. |
| 2003/0125619 A1 | 7/2003 | Manning et al. |
| 2003/0163139 A1 | 8/2003 | Graf |
| 2004/0059296 A1 | 3/2004 | Godfrey |
| 2004/0073193 A1 | 4/2004 | Houser et al. |
| 2004/0267203 A1 | 12/2004 | Potter et al. |
| 2005/0020981 A1 | 1/2005 | Kurth |
| 2005/0054984 A1 | 3/2005 | Polley et al. |
| 2005/0124937 A1 | 6/2005 | Kick et al. |
| 2005/0267487 A1 | 12/2005 | Christensen et al. |
| 2006/0030817 A1 | 2/2006 | Kraus et al. |
| 2006/0030864 A1 | 2/2006 | Kennedy, II et al. |
| 2006/0149293 A1 | 7/2006 | King et al. |
| 2006/0167417 A1 | 7/2006 | Kratz et al. |
| 2007/0060927 A1 * | 3/2007 | Longson et al. ............ 606/108 |
| 2007/0078438 A1 | 4/2007 | Okada |
| 2007/0225659 A1 | 9/2007 | Melsheimer |
| 2007/0293845 A1 | 12/2007 | Leeflang et al. |
| 2008/0082120 A1 | 4/2008 | Mauch et al. |
| 2008/0097386 A1 | 4/2008 | Osypka |
| 2008/0114335 A1 | 5/2008 | Flickinger et al. |
| 2008/0208128 A1 | 8/2008 | Guo et al. |
| 2008/0249558 A1 | 10/2008 | Cahill |
| 2009/0209972 A1 | 8/2009 | Loushin et al. |

* cited by examiner

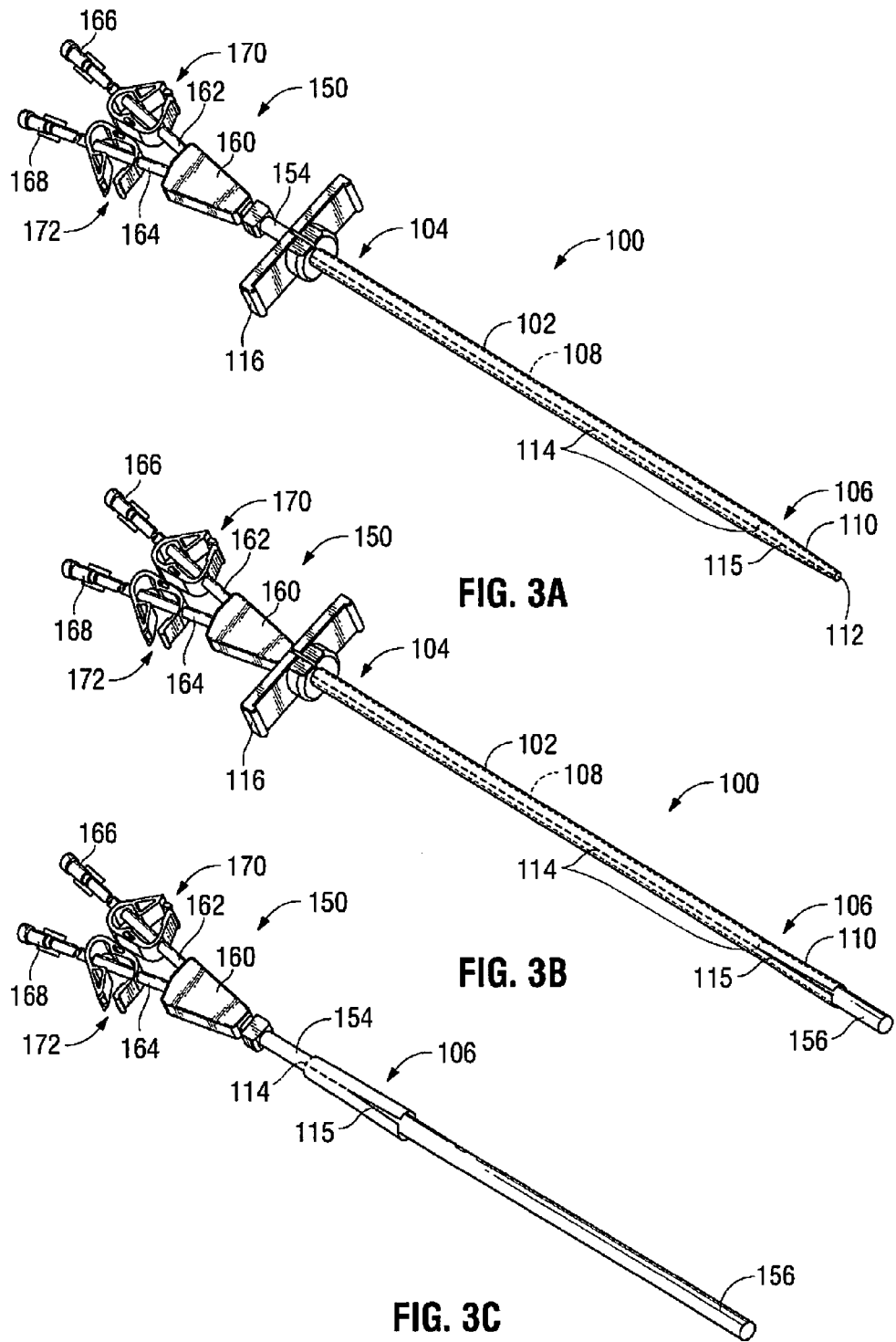

INTRODUCER SHEATH FOR CATHETERS

TECHNICAL FIELD

The present disclosure relates to catheter assemblies and, more particularly, to an introducer sheath for placement of a catheter into a body.

BACKGROUND

Catheters are flexible medical instruments for use in the withdrawal and introduction of fluids to and from body cavities, ducts, and vessels. Catheters have particular application in hemodialysis procedures, in which blood is withdrawn from a blood vessel for treatment and subsequently returned to the blood vessel for circulation through a patient's body. Catheters may also be used for other procedures and include central venous catheters, dialysis catheters, peripheral catheters and neurology catheters.

Various techniques are employed for the insertion of catheters into the body including, but not limited to, the use of guidewires, introduction stylets or obturators, dilator/sheath assemblies, and the like. For example, during such procedures, a hollow needle cannula may be inserted into a target vessel in, for example, the venous system, to create a venotomy (entry) site. Upon positioning the needle cannula within the target vessel, a guidewire is inserted through a proximal end of the needle cannula, into the target vessel, and advanced to a desired location within the target vessel. The needle cannula is then withdrawn, leaving a distal end of the guidewire positioned within the target vessel at the desired location, and a proximal end of the guidewire extending outwardly from the venotomy site. A dilator/sheath assembly is then threaded over the guidewire and into the vessel through the venotomy site to expand the venotomy site and target vessel to help insert the flexible catheter. The separate dilator within the sheath provides the structure at the distal end of the sheath to push through and expand the tissue. The guidewire and dilator are then retracted from the site, leaving the sheath in position. The sheath typically includes a hemostatic valve to reduce the loss of blood and the aspiration of air therethrough as the dilator is removed and before a catheter or other instrument is inserted into the sheath. A catheter may then be introduced through the hemostatic valve and sheath, and advanced into position within the target vessel at which time the sheath may be withdrawn from the vessel over the catheter such that the distal tip of the catheter remains in place within the vessel.

Although known insertion techniques have proven to be effective, it would be advantageous to provide a device to enable for the insertion of the catheter into the circulatory system without the need for a separate dilator/obturator or hemostatic valve, thereby reducing the number of insertion accessories, procedure time, and cost. Such a device would enable the successful insertion of catheters having various tip designs (e.g., blunted, non-tapered, or split tips) to be inserted directly into the vasculature with the sheath. The device would also enable the successful insertion of catheters fabricated from various materials as the device may be provided with varying degrees of stiffness. A stiffer device, for example, may replace the need to use a stylet during insertion of softer catheters thereby further reducing the cost of a catheter kit, the number of components a clinician has to interact with during a catheterization procedure, and the procedure time.

SUMMARY

The present introducer sheaths include a tubular body portion having a proximal region and a distal region and define an internal lumen configured and dimensioned to slidably receive a catheter. A penetrating portion at a distal end of the tubular body has a first tapered configuration to enlarge an opening in a body tissue during distal advancement of the introducer sheath through the body tissue and a second expanded configuration to enable the passage of a distal end portion of a catheter through the penetrating portion.

Methods of positioning a catheter within a body tissue are also described. In accordance with an embodiment of the present methods, a catheter assembly is provided. The catheter assembly includes a catheter disposed within a tubular body of an introducer sheath, the tubular body including a proximal region and a distal region including a penetrating portion having a first configuration which is tapered towards a distal opening. An opening in the body tissue is then dilated with the penetrating portion of the introducer sheath and the penetrating portion is expanded to a second configuration having a substantially uniform diameter to accommodate passage of the catheter therethrough.

BRIEF DESCRIPTION OF THE DRAWINGS

Various embodiments of the present disclosure will be described herein with references to the accompanying drawings, wherein:

FIGS. 3A and 3B are side, perspective views of the introducer sheath of FIG. 1 and the exemplary catheter of FIG. 2 in a first configuration and a second configuration, respectively;

FIG. 3C is a side, perspective view of the introducer sheath of FIG. 1 being maintained on the proximal end portion of the exemplary catheter of FIG. 2 in accordance with an embodiment of the present disclosure;

DETAILED DESCRIPTION OF THE EMBODIMENTS

Various exemplary embodiments of the present disclosure are discussed herein below in terms of medical catheters for the administration of fluids, such as withdrawal from and introduction to the body of a patient and, more particularly, in terms of catheters for vascular access. Vascular access catheters include, for example, central venous catheters, acute dialysis catheters, chronic dialysis catheters, and peripheral catheters. However, it is envisioned that the principles of the present disclosure are equally applicable to a range of catheter applications including surgical, diagnostic, and related treatments of diseases and body ailments of a patient. It is further envisioned that the principles relating to the presently disclosed catheter assemblies may be equally applicable to a variety of catheter related procedures, such as, for example, hemodialysis, cardiac, abdominal, urinary, and intestinal procedures, in chronic and acute applications. Moreover, the presently disclosed catheter assemblies can be used for administration and removal of fluids such as, for example, medication, saline, bodily fluids, blood and urine.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

The following discussion includes a description of the presently disclosed catheter assemblies and a description of an exemplary corresponding method of use in accordance with the principles of the present disclosure. For the purposes of discussion, the catheter, introducer sheath, and other components will be discussed in terms of a hemodialysis catheter, and the corresponding method of use will be discussed in terms of a procedure utilized for positioning a catheter into the circulatory system. However, those skilled in the art will appreciate the presently disclosed catheter assemblies, and the components thereof, have many other applications in addition to dialysis applications, such as those described above.

Figure 1:
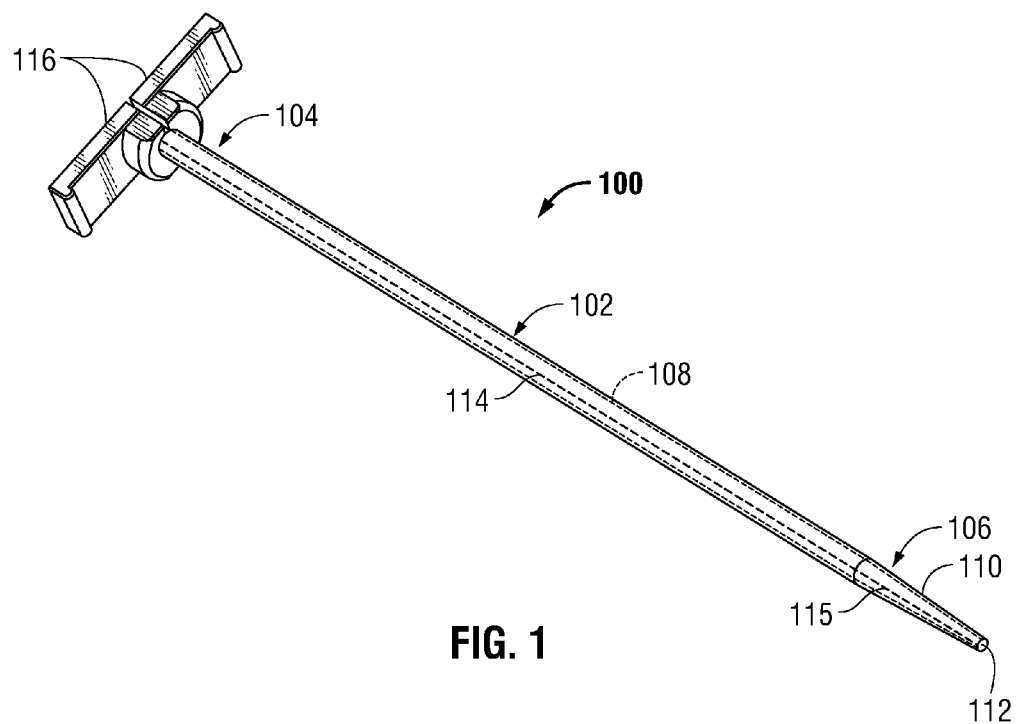
FIG. 1 is a side, perspective view of an introducer sheath in accordance with one embodiment of the present disclosure.
Figure 2:
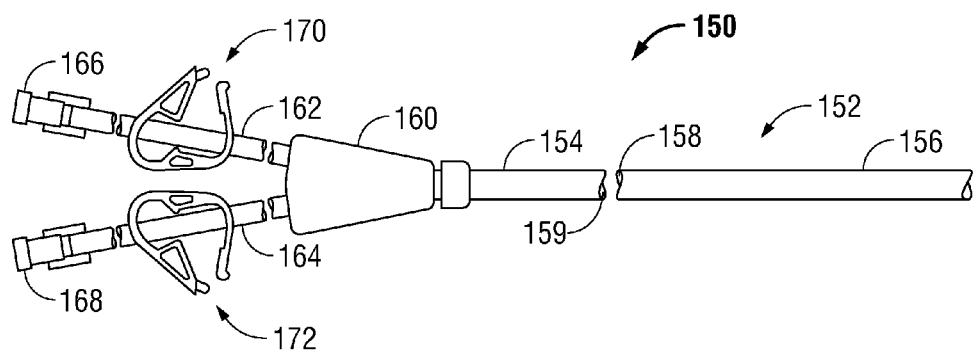
FIG. 2 is a side view of an exemplary catheter which may be utilized with the introducer sheath of the present disclosure.

Referring now to the figures, wherein like components are designated by like reference numerals throughout the several views, FIG. 1 illustrates one embodiment of an introducer sheath 100 for use in the placement of a catheter in a patient, such as the catheter 150 seen in FIG. 2. The introducer sheath 100 includes a tubular body portion 102 having a proximal region 104 and a distal region 106. The body portion 102 of the introducer sheath 100 defines an internal lumen 108 (shown in phantom in FIG. 1) that is configured and dimensioned to slidably receive the catheter 150 (FIG. 2).

The distal region 106 of the introducer sheath 100 includes a distally tapered penetrating portion 110 that is configured and dimensioned to enlarge an opening formed in target tissue, such as a venotomy site, during distal advancement of the introducer sheath 100. The penetrating portion 110 is fixedly secured to, or monolithically formed with, the body portion 102, and includes a distal opening 112 that is configured and dimensioned to receive a guidewire (not shown). In one embodiment of the introducer sheath 100, it is contemplated that the distal opening 112 may define an internal transverse dimension that substantially approximates an outer dimension of the guidewire to minimize the surface area at the distal-most end of the penetrating portion 110, and thereby minimize trauma to the patient's tissue during introduction of the introducer sheath 100 into a patient.

In the embodiment of the introducer sheath 100 illustrated in FIG. 1, the introducer sheath 100 includes one or more perforations 114, 115. The perforations 114 along the proximal region 104 may be, for example, diametrically opposed perforations to facilitate tearing or splitting of the introducer sheath 100. The perforations 115 along the distal region 106 may be the same or distinct from perforations 114 and also may include any number of additional rows of perforations to form the tapered configuration and facilitate expansion of the penetrating portion 110 of the introducer sheath 100. It should be understood that the placement and spacing of the perforations 114, 115 through the introducer sheath 100 may vary along the length of the tubular body 102. Specifically, following placement of the catheter 150 (FIG. 2) into the target tissue as desired, the clinician can tear, or split, the introducer sheath 100 along the perforation(s) 114 to facilitate separation of the introducer sheath 100 from the catheter 150 (FIG. 2). To facilitate such tearing, the introducer sheath 100 may include manual grips or members 116 positioned in the proximal region 104 of the introducer sheath 100 that are configured and dimensioned for manipulation by the clinician.

Referring now to FIG. 2, an exemplary catheter 150 which may be utilized with the presently disclosed introducer sheaths will be discussed. The catheter 150 will be discussed, and illustrated in the corresponding figures, as a dual lumen catheter. It should be appreciated, however, that the principles of the present disclosure are equally applicable to catheters having alternative tip configurations, such as staggered tip or split-tip, catheters including a single lumen or multiple lumens, such as triple lumen catheters, and other catheters of various cross-sectional geometries, and/or catheters that are employable in a variety of other medical procedures. For example, suitable non-exclusive examples of catheters falling within the scope of the present disclosure are the PALINDROME™ and MAHURKAR® Maxid™ catheters, each of which is made available by Covidien, which maintains a principal place of business at 15 Hampshire Street, Mansfield, Mass.

Catheter 150 includes elongate body 152, catheter hub 160, and extension tubes 162, 164. The elongate body 152 includes proximal end portion 154 and a distal end portion 156, and defines lumens 158, 159 through which fluid may be removed and/or returned to a patient's body. Lumens 158, 159 of elongate body 152 are adapted to be fluidly coupled to catheter hub 160. Extension tubes 162, 164 extend proximally from catheter hub 160 and may include adapters 166, 168, respectively, attached thereto for attachment to external devices. Clamps 170, 172 may also be positioned on extension tubes 162, 164, respectively, to control the flow of fluid through extension tubes 162, 164 by inhibiting or permitting the passage of fluid upon clamping or unclamping.

The introducer sheath 100 may be separately manufactured, such as by extrusion or molding, and inserted onto at least the distal end portion 156 of catheter 150 prior to packaging. Alternatively, introducer sheath 100 may be applied to the catheter 150 at any time prior to introduction into the target vessel, wherein introducer sheath 100 may be chosen such that the internal lumen 108 of the introducer sheath 100 may define an internal transverse dimension that substantially approximates an outer dimension of the elongate body 152 of catheter 150 thereby eliminating the need for the introducer sheath 100 to be valved at the proximal region 104. Alternatively, however, the introducer sheath 100 may include one or more hemostatic valves positioned within the internal lumen 108 that are configured and dimensioned to inhibit fluid communication through the introducer sheath 100. In embodiments, the hemostatic valve may be a self-sealing membrane through which a catheter may be introduced and removed without leakage of body fluids or introduction of air therethrough.

FIGS. 3A and 3B illustrate catheter 150 positioned within introducer sheath 100. In use, after placement of the guidewire within a target vessel as described above, the clinician will insert the guidewire (not shown) through the distal opening 112 of the introducer sheath 100 such that the guidewire may be passed through the distal end portion 156 of catheter 150, through lumen 158 (FIG. 2), and out of the proximal end portion 154 of the catheter 150, such as out of one of the extension tubes 162, 164. The penetrating portion 110 is provided in an initial tapered configuration so that the penetrating portion 110 may be introduced into an opening of the target vessel, such as the venotomy site, and expands the opening during distal advancement of the introducer sheath 100. After dilating the opening of the vessel and advancing the introducer sheath 100 to the desired position, the distal end portion 156 of the catheter 150 may then be distally passed through the distal region 106 of the introducer sheath 100 by applying a force to the catheter 150 in the distal direction to thereby break the perforations 115 in the sheath material of the penetrating portion 100 (as shown in FIG. 3B) and continuing to advance the catheter 150 until the catheter 150 is properly positioned within the vessel.

Alternatively, the penetrating portion 110 may be fabricated from any suitable material or combinations of materials which are sufficiently extendible, expandable, pliable, malleable, ductile, compressible, elastic, and/or rubbery to provide for controlled expansion of the distal opening 112 of the introducer sheath 100 upon passage of the catheter 150 therethrough, while maintaining sufficient stiffness for initial passage and dilation of the vessel. Examples of suitable materials include, for example, one or more moldable and/or thermoformable plastics, polymers, urethanes, natural or synthetic rubbers, silicones, elastomer and/or elastomeric or latex materials.

The proximal region 104 of the introducer sheath 100 may then be cracked along perforations 114 thereby breaking the perforations 114 in the sheath material until the introducer sheath 100 is separated into two separate pieces. The pieces may be removed by sliding the introducer sheath 100 proximally towards the catheter hub 160 of the catheter 150 until the material is completely removed from the insertion site. In other embodiments, the introducer sheath 100 may remain on the catheter 150, or only a portion of the introducer sheath 100 may be separated and removed via perforations 114, as shown in FIG. 3C, such that the introducer sheath 100 acts as a barrier between the patient's tissue and the catheter 150. Moreover, by maintaining the introducer sheath 100 or a portion thereof on the catheter 150, the introducer sheath 100 may function as a strain relief to increase the kink resistance of the catheter 150 adjacent proximal end portion 154 of catheter 150. Further still, the introducer sheath 100, or a portion thereof, may be treated with an antimicrobial material, or other medicaments, to help prevent infection at the venotomy site.

Figure 4A:
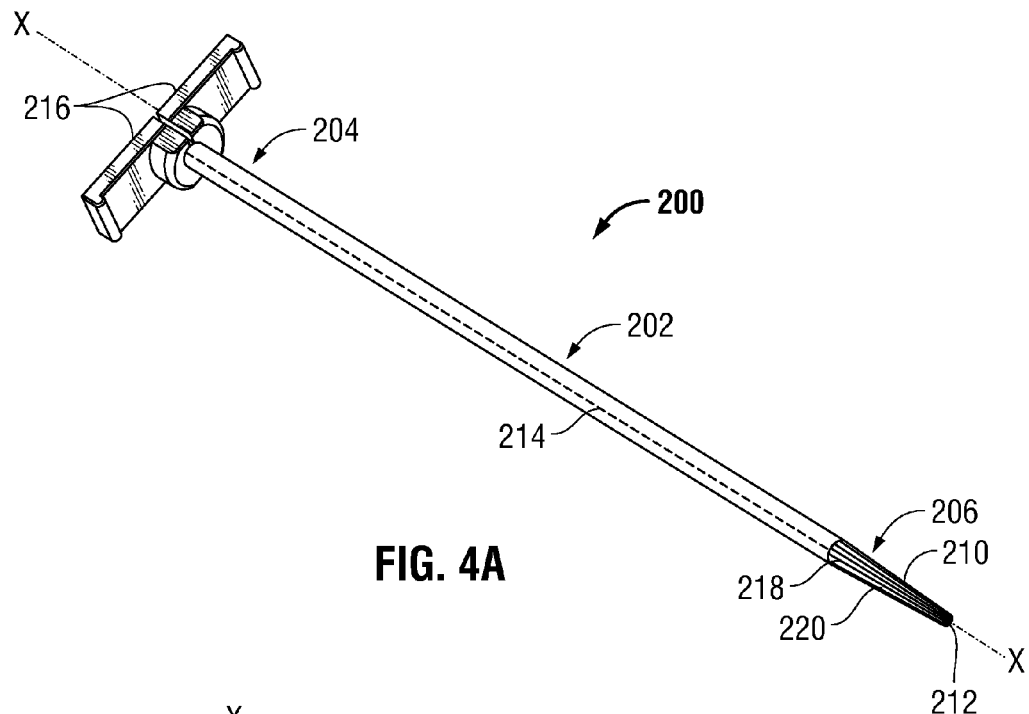
FIG. 4A is a side, perspective view of an introducer sheath in accordance with another embodiment of the present disclosure.
Figure 4B:
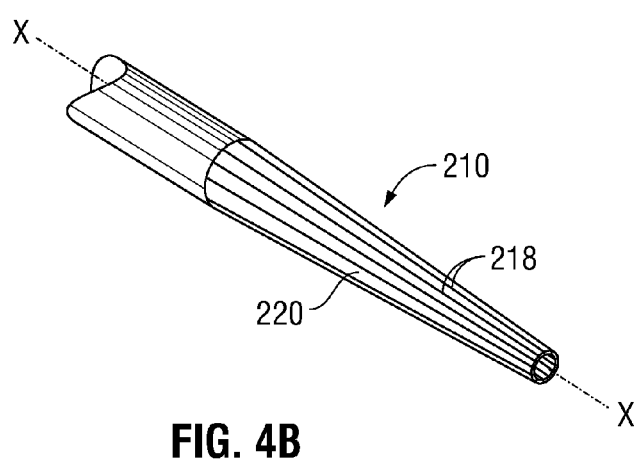
FIGS. 4B and 4C are close-up views of the distal region of the introducer sheath of FIG. 4A in a first configuration and a second configuration, respectively.

With reference now to FIGS. 4A and 4B, an introducer sheath 200 in accordance with another embodiment of the present disclosure is provided. The introducer sheath 200 is similar to the introducer sheath 100 discussed above with respect to FIG. 1, and accordingly, will only be discussed with respect to any differences therefrom.

Introducer sheath 200 includes a tubular body portion 202 having a proximal region 204 and a distal region 206. The body portion 202 of the introducer sheath 200 defines an internal lumen (FIG. 1) that is configured and dimensioned to receive a catheter, such as catheter 150 illustrated in FIG. 2. The lumen defines a central longitudinal axis "X". As discussed above in connection with the introducer sheath 100 (FIG. 1), introducer sheath 200 may include one or more perforations 214, such as diametrically opposed perforations, and manual grips or members 216 to facilitate tearing of the introducer sheath 200 along the perforation(s) 214.

The distal region 206 of introducer sheath 200 includes a penetrating portion 210 that may be cut at various locations around the distal opening 212 such that the cuts 218 form fingers 220 which are configured to nest in a tapered configuration towards the distal opening 212 by bending the fingers 220 inwardly towards the central longitudinal axis "X". In embodiments, the fingers 220 may extend over, overlie, overlap, or rest on one another. In other embodiments, the fingers 220 may lie next to and butt up against each other along cuts 218. The penetrating portion 210 of the distal region 206 has a first, or initial configuration in which a catheter does not extend therethrough and the fingers 220 are tapered to facilitate insertion of the penetrating portion 210 into a target vessel.

Figure 5A:
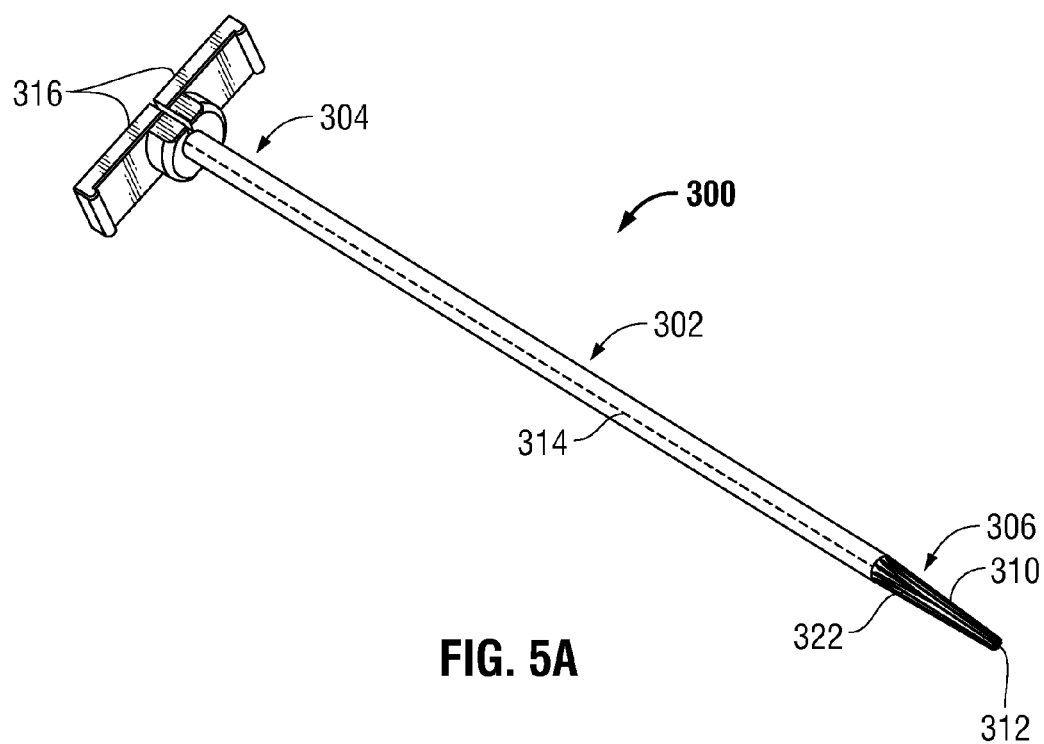
FIG. 5A is a side, perspective view of an introducer sheath in accordance with yet another embodiment of the present disclosure.
Figure 5B:
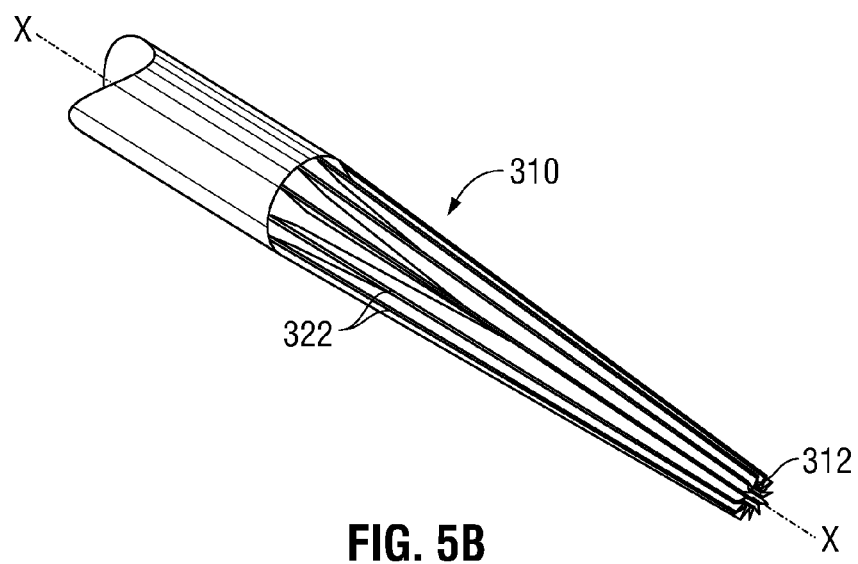
FIG. 5B is a close-up view of the distal region of the introducer sheath of FIG. 5A.

Alternatively, as illustrated in FIGS. 5A and 5B, distal region 306 of introducer sheath 300 may include at least one fold 322, or a plurality of folds 322, formed or extending radially thereabout such that distal region 306 tapers in a distal direction to a radially smaller diameter at or adjacent distal opening 312 to form penetrating portion 310. As used herein, the term "fold" is understood to include a pleat, undulation, corrugation, crease, bend and the like. Generally, the fold(s) 322 will be at or near distal opening 312 such that the material that is folded, bent or undulating, can open-up, unfold, extend or expand to enable a catheter to pass through the distal opening 312.

Figure 4C:
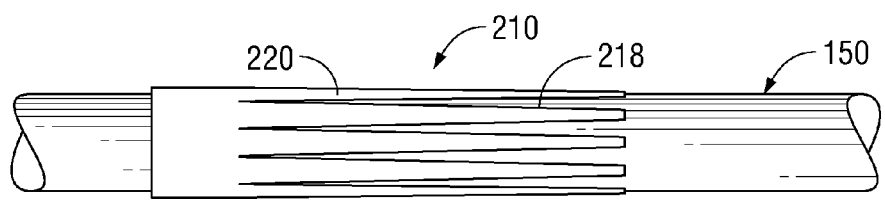

As shown in FIG. 4C, penetrating portion 210 may have one or more second, or subsequent configurations to accommodate the passage or extension of a catheter therethrough, in which the penetrating portion 210 is at least partially or fully extended or expanded to have a diameter which is substantially equal to the diameter of the lumen extending through body portion 202. As can be seen, as the catheter 150 is advanced through penetration portion 210, the fingers 220 split along cuts 218 and splay outwardly to expand distal opening 212 thereby enabling passage of catheter 150. It is envisioned that the penetrating portion 210, 310 can be temporarily secured into the tapered configuration using an adhesive that is capable of dissolving or softening and separating once inserted into the vasculature, such as a polymer based adhesive. For example, a polysaccharide-based adhesive could be employed that would weaken upon exposure to the body fluids of the patient's vasculature. Alternatively, the penetrating portion 210, 310 may be temporarily secured into the tapered configuration by heat setting the fingers 220 or folds 322. Further still, the fingers 220 or folds 322 may be thermally bonded together to form the tapered configuration such that the thermal bond may be broken and the penetrating portion 210, 310 expanded upon distal advancement of the catheter 150.

Figure 6A:
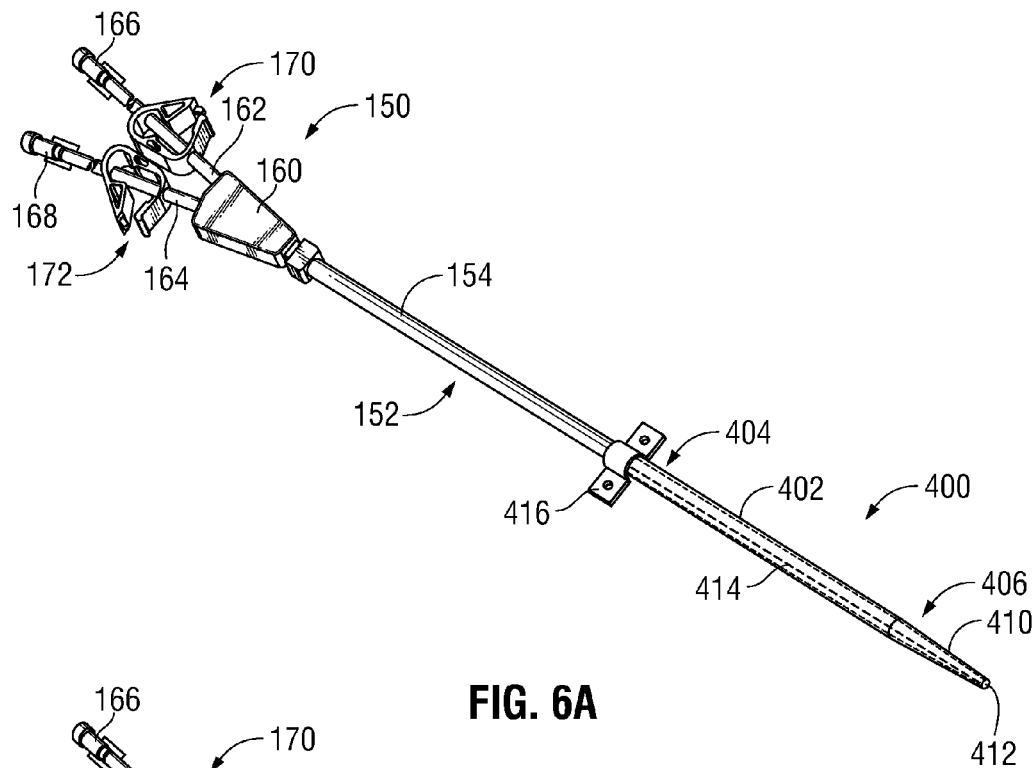
FIGS. 6A and 6B are side, perspective views of an introducer sheath in accordance with another embodiment of the present disclosure in a first configuration and in a second configuration, respectively.
Figure 6B:
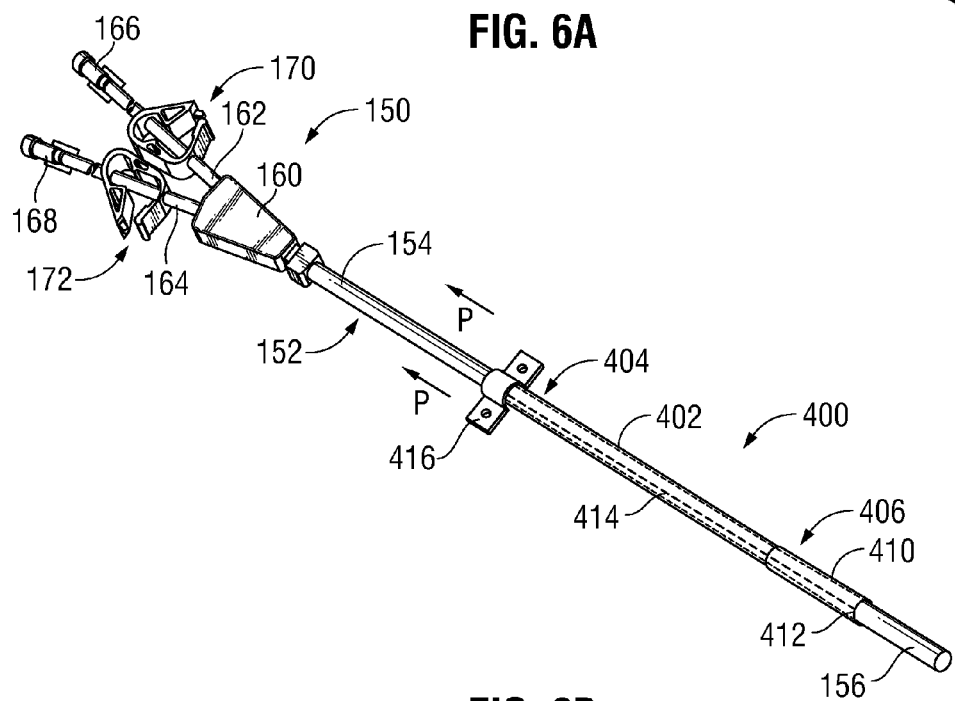

FIGS. 6A and 6B illustrate an introducer sheath 400 which is fabricated, at least in part, from materials which are capable of adopting a shape in-vivo to aid in the insertion, placement, use, and withdrawal of a catheter in accordance with the present disclosure. In embodiments, shape memory polymeric materials may be utilized to form the introducer sheath 400 of the present disclosure which possesses a permanent shape at body temperature and a temporary shape at room temperature.

Shape memory polymers are a class of polymers that, when formed into an object such as an introducer sheath, can be temporarily deformed by mechanical force and then caused to revert back to an original shape when stimulated by energy, such as heat, light, or electrical current. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which the shape change occurs during heating. The shape memory polymers can thus be tailored by altering material properties at the molecular level and by varying processing parameters. An object's primary shape may be formed with heat and pressure at a temperature at which the soft domains are flexible and the hard domains are not fully formed. The object may then be cooled so that the hard domains are more fully formed and the soft domains become rigid. The secondary or temporary shape can be formed by mechanically deforming the object, which is most readily accomplished at a temperature approaching or above $T_{Trans}$. Mechanical stresses introduced into the object are then locked into place by cooling the object to temperatures below $T_{Trans}$, so that the soft segments solidify to a rigid state. Once the object is heated to $T > T_{Trans}$, the soft segments soften and relax back to their original configuration and the object returns to its primary shape, sometimes referred to herein, as its permanent shape. The temperature at which a shape memory material reverts to its permanent shape may be referred to, in embodiments, as its permanent temperature ($T_{perm}$).

Polymers possessing shape memory properties which may be used to construct introducer sheaths in accordance with the present disclosure include biocompatible and non-biodegradable materials. In embodiments, the shape memory polymer may be a copolymer of different biocompatible materials, such as materials having different thermal characteristics. In embodiments, the shape memory polymer may be a blend or mixture of two or more materials to create a polymeric material having the desired physical properties. Other shape memory materials, including shape memory metals and metal alloys such as Nitinol, may also be used to form the introducer sheaths of the present disclosure.

In embodiments, the shape memory material is a crosslinked polyurethane made by using excess diisocyanate or by using a crosslinker such as glycerin or trimethylol propane. However, other suitable non-degradable materials may be employed, so long as the $T_{trans}$ temperature is between room and body temperatures. Specifically, it is desired that at least a penetrating portion 410 be harder at room temperature and softer, or pliable, at body temperature and relax to a permanent shape through which the catheter 150 may pass.

As illustrated in FIGS. 6A and 6B, introducer sheath 400 includes a tubular body portion 402 having a proximal region 404 and a distal region 406. The body portion 402 of the introducer sheath 400 defines an internal lumen (FIG. 1) that is configured and dimensioned to receive a catheter, such as catheter 150. As discussed above in connection with the introducer sheath 100 (FIG. 1), introducer sheath 400 may include one or more perforations 414, and manual grips or members (not shown) to facilitate tearing of the introducer sheath 400 along the perforation(s) 414. Alternatively, introducer sheath 400 may include suture wing 416 to secure introducer sheath 400 to the patient in embodiments in which introducer sheath 400 is left on the catheter 150 as a strain relief and/or antimicrobial barrier.

At least the distal region 406 of the introducer sheath 400 is fabricated from a shape memory polymeric material which is compressed into a temporary shape such that the penetrating portion 410 tapers to the distal opening 412. Transformation from the temporary shape to the permanent shape, as illustrated in FIG. 6B, such as by placement within a patient's body to heat the shape memory polymeric material, results in the radial expansion of the penetrating portion 410 to enable the catheter 150 to pass therethrough.

The proximal region 404 of the introducer sheath 400 may then be cracked along the perforations 414 to remove the introducer sheath 400 from catheter 150. Alternatively, the introducer sheath 400 may slide proximally in the direction of arrows "p" towards the catheter hub 160 to retain the introducer sheath 400 on the catheter 150 as discussed above and sutured in place using suture wings 416. In embodiments, catheter hub 160 may include fastening means, such as hooks, detents, or snaps, to facilitate the retention of the introducer sheath 400 in contact with the hub 160 of catheter 150. It is envisioned that body portion 402 of the introducer sheath 400 may vary in length depending on the type of catheter that is to be inserted therethrough and the particular surgical application in which the particular device is going to be used, such as removing the introducer sheath 400 or retaining at least a portion of the introducer sheath 400 on the catheter 150.

In embodiments, a molding process may be utilized to produce an introducer sheath 400 of the present disclosure. Plastic molding methods are within the purview of those skilled in the art and include, but are not limited to, melt molding, solution molding, and the like. Injection molding, extrusion molding, compression molding and other methods can also be used as the melt molding technique. Once placed in the mold with the proper dimensions and configuration, the polymeric material used to form the introducer sheath may be heated to a suitable temperature (e.g., the permanent temperature ($T_{perm}$)), which may, in embodiments, be the melting temperature of the shape memory polymeric material utilized to form the introducer sheath. Heating of the introducer sheath may be at suitable temperatures for a period of time sufficient to obtain the permanent shape and dimensions.

The temperature for deformation treatment of the introducer sheath molded with a previously memorized shape is one that makes possible ready deformation without producing cracks and should not exceed the temperature adopted for the shape memorization (e.g., $T_{perm}$). Deformation treatment at a temperature exceeding that for the original shape memorization may cause the object to memorize a new permanent shape.

After an introducer sheath with the desired shape has been formed, the introducer sheath may be deformed at a deforming temperature to obtain an alternate, temporary shape.

Suitable temperatures for deformation will vary depending on the shape memory polymer utilized, but generally may be above the transition temperature of the polymer ($T_{trans}$), but below the $T_{perm}$. In embodiments, the shape memory polymer may be cooled from its $T_{perm}$ to a lower temperature which remains above the $T_{trans}$ and deformed, in embodiments by hand and/or mechanical means. There are no particular limitations on the manner in which deformation can be achieved. In other embodiments, the introducer sheath may be deformed to room temperature (about 20° C. to about 25° C.) to obtain its temporary shape, although the temperature may differ depending upon the particular polymer employed. The introducer sheath may then be cooled to a temperature below the $T_{trans}$ of the material utilized to form the introducer sheath, at which time the introducer sheath of the present disclosure is ready for use. As the $T_{trans}$ is usually greater than room temperature, in embodiments cooling to room temperature may be sufficient to form the temporary shape.

The introducer sheaths thus prepared recover their originally memorized shape upon application of energy, such as heating, either by placement in a patient's body and heating with body heat (about 37° C.), or the addition of exogenous heat at a prescribed temperature, in embodiments above the $T_{trans}$ of the shape memory polymer utilized. The higher the temperature for heating, the shorter the time for recovery of the originally memorized shape. In embodiments in which a higher shape memory temperature is desired, heating can be accomplished by using a gas or liquid heating medium, heating devices, ultrasonic waves, electrical induction, chemical reaction, and the like. The means for this heating, however, is not limited. Of course, in an application involving a living body, care must be taken to utilize a heating temperature which will not cause burns. Examples of liquid heating media include physiological saline solution, alcohol, combinations thereof, and the like.

As described above, medicinal agents may be incorporated into or provided on the various disclosed introducer sheaths. Medicinal agents that may be incorporated into or provided on the disclosed introducer sheath and/or on an internal surface of the lumen of the introducer sheath may include antimicrobial agents, anti-virals, anti-fungals, anti-thrombogenics, anti-stenotics and the like, and combinations thereof. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, and combinations thereof.

Methods for combining medicinal agents with an introducer sheath of the present disclosure are within the purview of those skilled in the art and include, but are not limited to, coating, compounding, spraying, wicking, solvent evaporating, dipping, brushing, vapor deposition, coextrusion, capillary wicking, film casting, molding and the like. It is envisioned that the medicinal agent may be applied to the present introducer sheath in any suitable form of matter, for example, films, powders, liquids, gels and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the invention based on the above-described embodiments. Accordingly, the invention is not to be limited by what has been particularly shown and described, except as indicated by the appended claims.

What is claimed is:

1. An introducer sheath comprising:
   a tubular body portion having a proximal region and a distal region and defining an internal lumen configured and dimensioned to slidably receive a catheter; and
   a penetrating portion at a distal end of the tubular body portion having a first tapered configuration to enlarge an opening in a body tissue during distal advancement of the introducer sheath through the body tissue and a second expanded configuration to enable the passage of a distal end portion of a catheter through the penetrating portion, the penetrating portion being separable from the tubular body portion via perforations and configured to be maintained on the catheter to act as a barrier between body tissue and the catheter and to increase a kink resistance of the catheter adjacent a proximal end portion of the catheter.

2. The introducer sheath of claim 1, wherein the introducer sheath further comprises perforations along at least a portion of the tubular body to facilitate removal of the sheath from the catheter.

3. The introducer sheath of claim 2, wherein the perforations formed in the proximal region are different from the perforations formed in the distal region of the tubular body.

4. The introducer sheath of claim 1, wherein the penetrating portion further comprises perforations, wherein the perforations break upon transition from the first configuration to the second configuration as the catheter is advanced towards the distal region.

5. The introducer sheath of claim 1, further comprising a medicinal agent coated on at least a portion of the introducer sheath.

6. The introducer sheath of claim 1, further comprising manual grips proximate to the proximal region.

7. The introducer sheath of claim 1, wherein the penetrating portion terminates in a blunt distal opening.

\* \* \* \* \*